United States Patent [19]

Heimburger et al.

[11] 4,245,039

[45] Jan. 13, 1981

[54] STABLE CLUMPING FACTOR FOR THE IDENTIFICATION OF FIBRINOGEN AND FIBRIN CLEAVAGE PRODUCTS AND PROCESS FOR PREPARING IT

[75] Inventors: Norbert Heimburger; Friedrich Brauns, both of Marburg an der Lahn; Kurt Fischer, Unterrosphe, all of Fed. Rep. of Germany

[73] Assignee: Behringwerke AG, Marburg an der Lahn, Fed. Rep. of Germany

[21] Appl. No.: 693,906

[22] Filed: Jun. 8, 1976

[30] Foreign Application Priority Data

Jun. 10, 1975 [DE] Fed. Rep. of Germany ....... 2525804

[51] Int. Cl.$^3$ .......................... C12Q 1/56; C12N 1/20; C12R 1/445
[52] U.S. Cl. ..................................... 435/13; 435/253; 435/260; 435/883
[58] Field of Search .............. 195/59, 56, 52, 65, 195/96, 103.5 R, 100; 424/92, 87, 12, 8, 2; 23/230 B; 435/253, 260, 883, 13, 4

[56] References Cited

U.S. PATENT DOCUMENTS

| | | | |
|---|---|---|---|
| 3,843,453 | 10/1974 | Freake | 195/103.5 R |
| 3,853,710 | 12/1974 | Innerfield | 195/103.5 R X |
| 3,983,004 | 9/1976 | Trobish et al. | 195/103.5 R |
| 3,990,947 | 11/1976 | Butler et al. | 195/103.5 R |

OTHER PUBLICATIONS

Hawiger et al., "Measurement of Fibrinogen and Fibrin Degradation Products in Serum by Staphylococcal Clumping Test", *J. Lab. Clin. Med.,* vol. 75, No. 1, pp. 93–108, (1970).

Duthie, "The Action of Fibrinogen on Certain Pathogenic Cocci", *J. Gen. Microbiol.,* vol. 13, pp. 383–393, (1955).

Thomas et al., "A Comparative Study of Four Methods for Detecting Fibrinogen Degradation Products in Patients with Various Diseases", *The New England Journal of Medicine,* vol. 283, No. 13, pp. 663–668, (1970).

Microbiology Abstracts, 3A (1967.12) 3, p. 124.

*Primary Examiner*—Thomas G. Wiseman
*Attorney, Agent, or Firm*—Curtis, Morris & Safford

[57] ABSTRACT

A homogeneous suspension, in a buffered aqueous solution having a pH of 7.0 to 7.7, of a destroyed microorganism which is positive to the clumping factor, said suspension containing from 3 to 50 percent by weight of at least one polyhydric alcohol soluble therein, is disclosed, as are its manufacture and its use as a reagent for the determination of fibrinogen and for fibrin cleavage products.

1 Claim, No Drawings

STABLE CLUMPING FACTOR FOR THE IDENTIFICATION OF FIBRINOGEN AND FIBRIN CLEAVAGE PRODUCTS AND PROCESS FOR PREPARING IT

This invention relates to a storable stable clumping factor suitable as reagent for the identification of fibrinogen and fibrin cleavage products and to a process for preparing it.

The activation of the fibrinolytic system leads to a proteolytic decomposition of fibrinogen or fibrin. During the decomposition of the fibrinogen, the so-called fragment X is formed first, and then further cleavage products are obtained which are designed by A, B and C. With regard to size and properties the fragment X bears the greatest analogy to fibrinogen and may slowly be brought to coagulation with thrombin. With a progressive proteolytic decomposition of the fragment X, there are formed the fragments Y and D. The fragment Y is no longer brought to coagulation with thrombin. A further proteolysis of the fragment Y leads to the split products D and E. The smaller split products D and E do not show all antigenic determinants of fibrinogen. The fibrin cleavage products are indicators for certain diseases and partly inhibitors for the formation of fibrin, so that it is interesting on a clinical scale to determine the content of fibrinogen and/or fibrin cleavage products and thus, the extent of an intraversal fibrinolysis.

A process for the determination of the cleavage products mentioned is based on the fact that certain microorganisms, especially strains of staphylococci, reach with fibrinogen and the fibrin cleavage products X and Y with macroscopically visible clumping. The property of clumping staphylococci is attributed to a cell-linked enzyme which is characterized only insufficiently. It is designed as "clumping factor". Sometimes it also stands for cell-linked coagulase. The rapidity with which it may be used and the high sensitivity of the test system based on the clumping factor, especially for the determination of fibrin cleavage products X and Y, renders this test system particularly suitable for the routine detection of fibrinolysis.

It has appeared, however, that the suspensions of suitable staphylococci prepared according to the state of the art maintain the necessary activity for the identification of the fibrin cleavage products for only a few hours and that the products, if freeze-dried in order to conserve the activity, may frequently not be suspended homogeneously in a solution, or clump unspecifically. The sensitivity of the resuspended germs decrease rapidly. After a few hours they are unsuitable as reagent for the identification of fibrin cleavage products.

It has now been found that clumping factor positive microorganisms, especially staphylococci, which are suspended in a buffered aqueous solution of a polyhydric alcohol do not lose their property of clumping in the presence of fibrinogen- and/or fibrin cleavage products even after a storage for several months at temperatures below +25° C.

The invention therefore relates to a homogeneous suspension of destroyed clumping factor positive microorganisms, preferably staphylococci, in a buffered aqueous solution having a pH value of 7.0 to 7.7 and containing a polyhydric alcohol dissolved therein in a concentration of 3 to 50%.

The use of *Staphylococcus aureus* Newman $D_2C$ has often been described for the test system in question. The strain concerned is a clumping factor-positive, soluble coagulase-negative varient of the strain Newman which has been selected with regard to the formation of clumping factor by E. S. Duthie, Southampton, from cultures of *Staphylococcus aureus* Newman, deposited at the National Collection of Type Cultures under the number 8178.

Clumping factor positive strains which are additionally capable of forming soluble coagulase can also be used for the determination of fibrin cleavage products—as is known from the literature—if the soluble coagulase is destroyed, for example by a heating step. Staphylococci pre-treated in such manner may also be stabilized according to the invention. Especially favorable results with regard to sensitivity and stability of the reagent for the identification of fibrinogen and fibrin cleavage products are provided by a *Staphylococcus aureus* having the designation I. J. 7 deposited at the American Type Collection under the number ATCC 31153, the morphology of which may be described in the following way. The strain was originally isolated from a human throat swab and selected with regard to the formation of cell-linked coagulase. In liquid nutrient media the strain grows in small groups or in pairs with a proportion of up to about 30% as individual cell colonies. The strain may be colored with the usual analine dyestuffs. It is gram-positive.

The characteristics of the *Staphylococcus aureus* I. J. 7 on the following solid nutrient media are the following ones:

|  | for isolation (24 hours, 37° C.) | for identification (24 hours, 37° C.) |
|---|---|---|
| Staphylococcus Medium 110 (Baltimore Biological Lab.) | good growth, yellowish colonies having a diameter of about 1 mm | |
| Horse blood - agar | good growth, grey colonies without hemolysis | |
| Nutrient agar | yellowish colonies sometimes irregularly developed due to rapid growth | |
| Purple-horse serum agar | faint yellow colonies having a diameter of 1.3 mm. Moderately coherent growth | |
| MacConcey-Agar No. 3 (oxoide) | no growth | |
| C.L.E.D. agar | | pale yellow colonies on slightly yellow ground |
| DNase agar | | yellowish colonies. No |

| for isolation (24 hours, 37° C.) | for identification (24 hours, 37° C.) |
| --- | --- |
| | flowing growth. After acidification with 1N HCl a slight DNase activity is detectable |

The strain *Staphylococcus aureus* I. J. 7 shows the following metabolism output:

| Fermentation of: | | | |
| --- | --- | --- | --- |
| dextrose | + | after 6 days | at 37° C. |
| lactose | + | after 6 days | at 37° C. |
| saccharose | + | after 6 days | at 37° C. |
| maltose | + | after 6 days | at 37° C. |
| mannitol | + | after 6 days | at 37° C. |
| salicin | − | after 13 days | at 37° C. |
| inulin | − | after 13 days | at 37° C. |
| aesculin | − | after 13 days | at 37° C. |
| Liquifaction | | | |
| gelatin | + | after 13 days | at 22° C. and 37° C. |

Already in the fermentation process according to which the bacterial mass is obtained, care has to be taken that the germs have a good capacity for suspension and that the yield with regard to the clumping activity is sufficient. Thus, it is expedient to effect the reproduction of the germs in a medium which essentially consists of an aqueous solution of meat peptone, lactic acid or the salts thereof, vitamins and glucose, alkali metal and alkaline earth metal ions, preferably in the form of their physiologically acceptable salts such as chlorides, sulfates and phosphates. The germs multiplied in bottles, kettles or fermenters, separated from the nutrient medium by filtration or centrifugation, are hindered in their reproduction by measures which reduce the activity of the clumping factor to the smallest possible extent. In proved and known manner the germs are destroyed by heating to about 60° to 70° C. for 30 to 90 minutes.

The essential stabilizing effect of the suspension of staphylococci which are active to the clumping factor according to the invention is due to the content of the suspension medium of 3 to 50% of a polyhydric alcohol. In the sense of the present invention these are compounds which—in a hydrocarbon skeleton, preferably an aliphatic hydrocarbon skeleton—carry one hydroxyl group on each one of several adjacent carbon atoms and which have a range of molecular weight of about 90 to about 500,000. The simplest compounds of this class of substances are the bivalent alcohol glycol and the trivalent alcohol glycerol. Advantageous stabilizing effects are shown, for example, by representatives of the hexavalent alcohols such as mannitol and of the carbohydrates such as glucose. Besides the low molecular weight compound, higher molecular weight glycols such as polyethylene glycol may also be used according to the invention for stabilization of the suspension. Furthermore, carbohydrates of both natural and synthetic origin, particularly high molecular weight representatives thereof, have particularly advantageous properties. Examples are the naturally-ocurring glucose polymer dextran or the synthetic polysaccharide from raw sugar which is available in commerce as Ficoll ® (trade mark of Messrs. Pharmacia Uppsala).

A prerequisite for the polyhydric alcohols to be used is their solubility in a buffered aqueous solution to which, if desired, neutral salts may be added in order to prepare an approximately isotonic medium for the microorganism cells to be suspended.

The suspension of the staphylococci is adjusted to the pH value desired, expediently with the aid of a buffer substance as it is normally used in biochemical operations. Suitable buffer substances are for example those described by Good and others in Biochemistry 5, 472 (1966). The concentration of the bacteria suspended in the buffered aqueous solution containing the polyhydric alcohol is $1-20\times10^{10}$/ml if the staphylococci suspension shall be directly used in test processes for the determination of fibrinogen- and/or fibrin cleavage products. But the stability of the clumping factor is also ensured if the germ concentration is considerably increased or reduced with regard to the value indicated.

The invention further relates to a process for the stabilization of the clumping factor linked to microorganisms wherein clumping factor forming microorganisms, preferably staphylococci, which are cultured according to a known process and are destroyed while maintaining the clumping factor, are suspended homogeneously in an aqueous solution buffered to pH 7.0 to 7.7, preferably 7.3 to 7.5, having a content of 3 to 50% of a polyhydric alcohol. Of course, there is no obstacle which would prevent the addition, to the microorganism suspension stabilized according to the invention, of further substances known from biochemistry, especially enzyme chemistry, which maintain or activate the enzymatic activity, such as proteins, especially albumin or gelatin decomposition products. To avoid a microbial contamination, an antimicrobial agent, for example an antibiotic, may be added to the suspension.

The invention further relates to a reagent for the identification of fibrinogen- and/or fibrin cleavage products, which reagent contains as an essential constituent $1-20\times10^{10}$ germs/ml of homogeneously suspended clumping factor positive microorganisms in a buffered aqueous solution containing a polyhydric alcohol, and to a process for preparing the reagent.

The invention finally relates to the use of a stable suspension of staphylococci for the determination of fibrinogen- and/or fibrin cleavage products in body liquids, preferably in plasma or serum, according to known processes. The determination of the fibrinogen- and/or fibrin cleavage products is carried out in the following way: the serum to be tested, from which a dilution series is established, is mixed with a constant, preferably an equal, amount of the suspension of staphylococci according to the invention, after which within a few minutes the highest serum dilution which just shows a positive clumping of the germs is observed. If this value is correlated with a value obtained by dilution of the serum of healthy persons, the result can be considered for deviation from the normal value.

The determination is carried out in known manner in the simplest way on a slide on which the reactants are mixed equally.

The following Example illustrates the invention.

EXAMPLE

Preparation of the Germ Suspension

*Staphylococcus aureus* I. J. 7 (ATCC 31153) is multiplied to a concentration of $15 \times 10^8$ germs per ml in a medium having the following

| composition | |
|---|---|
| meat peptone | 80.0 g |
| sodium lactate solution, 50% | 25.0 ml |
| ammonium chloride | 18.5 g |
| magnesium sulfate (7H$_2$O) | 0.8 g |
| dipotassium hydrogen phosphate | 4.0 g |
| potassium dihydrogen phosphate | 4.0 g |
| diluted up with water to 4 liters and provided with the following additives: | |
| D (+) biotin | 0.02 mg |
| calcium-D(+)-pantothenate | 1.00 mg |
| choline chloride | 0.08 mg |
| folic acid | 0.20 mg |
| maso-inositol for biochemical and microbiological purposes | 0.08 mg |
| nicotinic acid | 6.00 mg |
| pyridoxal-hydrochloride | 0.50 mg |
| riboflavin | 0.72 mg |
| thiamine dichloride | 2.448 mg |
| glucose | 10 g |

Then the fermenter in which the multiplication has taken place is heated for 90 minutes to 70° C. The germs are obtained with the aid of a centrifuge at 6,500 rpm. The supernatent nutrient medium is rejected, and the germs are suspended repeatedly in an isotonic sodium chloride solution and centrifuged. Finally the centrifuged germs are suspended in a buffer solution having the following composition:
0.1 M/l of tris-hydroxymethyl-aminomethane
0.3 M/l of sodium chloride
0.02% of chloroamphenicol
0.02% of human albumin.
The pH value of the solution is adjusted to 7.4 with 1 N hydrochloric acid, after which one part by volume of glycerol is added to one part by volume of the buffer solution. Then the germ concentration of the suspension is adjusted to $1 \times 10^{11}$/ml.

In the following test system the suspension obtained shows a constant result over 12 months:

1. Obtention of a Serum from a Healthy Normal Person 5 ml of freshly taken blood are carefully mixed with 0.1 ml of a polyvalent proteinase inhibitor corresponding to 10 antiplasmin units and 0.1 ml of a thrombin solution corresponding to 10 NIH units. The mixture is incubated for 2 hours at 37° C. and subsequently the supernatent serum is separated from the blood coagulum by centrifugation.

2. Test Preparation Mixture

Using 0.1 M of tris-hydroxymethyl-aminomethane-hydrochloric acid buffer having a pH value of 7.4, a geometric dilution series of the serum is prepared so that a dilution of 1:1, 1:2, 1:4, 1:8 etc. results therefrom. In each case 0.05 ml of the serum dilutions is mixed on a slide with 0.05 ml of the suspension of staphylococci prepared according to the above-mentioned Example. The mixture is allowed to rotate cautiously and the clumping reaction is read off against a black background. A clumping up to a dilution of 1:256 may be detected. The same result is obtained if the buffer used is not mixed with 50% of glycerol, as indicated in the Example, but with the following substances.

| Substance | weight % | molecular weight |
|---|---|---|
| glycerol | 33 | 92 |
| glucose | 10 | 180 |
| mannitol | 3 | 182 |
| mannitol | 10 | 182 |
| mannitol | 15 | 182 |
| polyethylene glycol | 3 | 4,000 |
| polyethylene glycol | 10 | 4,000 |
| dextran | 3 | 40,000 |
| dextran | 10 | 40,000 |
| dextran | 3 | 250,000 |
| dextran | 10 | 250,000 |
| Ficoll | 3 | 70,000 |
| Ficoll | 10 | 70,000 |
| Ficoll | 3 | 400,000 |
| Ficoll | 10 | 400,000 |

What we claim is:

1. A homogeneous suspension of non-viable *Staphylococcus aureus* I. J. 7, positive to the clumping factor, in a buffered aqueous solution having a pH from 7.0 to 7.7 and containing from 3 to 50 percent by weight of at least one polyhydric alcohol soluble therein.

* * * * *